United States Patent [19]
Liu

[11] Patent Number: 5,917,096
[45] Date of Patent: Jun. 29, 1999

[54] PROCESS FOR THE PREPARATION OF β-CARYOPHYLLENE ALCOHOL

[75] Inventor: Hongjun Liu, Jiangsu, China

[73] Assignee: Research Institute of Chemical Processing and Utilization of Forest Products, China

[21] Appl. No.: 08/793,568

[22] PCT Filed: Aug. 31, 1994

[86] PCT No.: PCT/CN94/00068

§ 371 Date: Jun. 16, 1997

§ 102(e) Date: Jun. 16, 1997

[87] PCT Pub. No.: WO96/06818

PCT Pub. Date: Mar. 7, 1996

[51] Int. Cl.$^6$ .................................................... C07C 35/23
[52] U.S. Cl. .............................................................. 568/819
[58] Field of Search ............................................. 568/819

[56] References Cited

U.S. PATENT DOCUMENTS 4,229,599  10/1980  Mussinan et al. .
4,267,076   5/1981  Mookherjee et al. .

OTHER PUBLICATIONS

March Textbook of Advanced Organic Chemistry Reactions Mechanisms and Structure. pp. 581–582 –(1968).
CA 116. 524 "Pharmacologic Studies on β Caryophyllene Alcohol, Tang" Zhongguo Yaolixue Tonglao (1991) 7(12), 145–8.
CA 121 129933 "Chemical Characteristics of Oleoresins of Some Exotic Pines", Song Linchan Huaxire Yu Gongyl (1993) 13(14), 277–87.
CA 120, 265848 "Chemical Constitiuants of Oleoresin From Main Chinese Pine Species" Su, Linchen Huaxule Yu Gongup 1993 13(Zengkan) pp. 33–40.
CA 109:129325 "Aromate Chemicals from Ingifolene" Kichukna, Pollena, Tluszcze, Srodki Procace, Kramet.

*Primary Examiner*—Gary Geist
*Assistant Examiner*—Jean F Vollano
*Attorney, Agent, or Firm*—Eugene Stephens & Associates

[57] ABSTRACT

The present invention discloses a new process for the preparation of β-caryophyllene alcohol, in which the sesquiterpene fraction at 110–120° C./6 mmHg in Chinese pinus massoniana oleoresin composition undergoes isomerization in the presence of sulfuric acid as catalyst and the β-caryophyllene alcohol is thus prepared through separation, re-crystallization and purification of the residue from the bottom of the vessel for the preparation of isolongifolene.

3 Claims, No Drawings

PROCESS FOR THE PREPARATION OF β-CARYOPHYLLENE ALCOHOL

This application is a 371 and the National Stage PCT/CN9400068 filed Aug. 31, 1994.

FIELD OF THE INVENTION

The present invention relates to a new process for the preparation of β-Caryophyllene alcohol.

BACKGROUND OF THE INVENTION

β-Caryophyllene alcohol is an important tricyclic sesquiterpenol, which can be widely used in perfumery and pharmaceutical industries. At present, β-caryophyllene alcohol is prepared through the hydration of β-caryophyllene. As disclosed in JP 01, 268, 657, β-caryophyllene alcohol is prepared by utilizing the β-caryophyllene as presented in mint oil. In addition, β-caryophyllene alcohol can also be prepared from a small amount of β-caryophyllene separated from cloveoil, copaihaoil, lavenderoil and bluinea oil, vitex cannabifolia oil from Chinese Compositae plants.

The sesquiterpene composition in Chinese pinus massoniana oleoresin contains longifolene, β-caryophyllene, cyclo-longifolene and longipinene. Among them, the β-caryophyllene content accounts for 13–17% of the composition. However, since its chemical configuration is very similar to the others and their differences in boiling points are only within 2° C., it is very difficult to conduct the separation process for obtaining β-caryophyllene alcohol in commercial practice.

The object of the present invention is to provide a new process for the preparation of β-caryophyllene alcohol from the β-caryophyllene contained in sesquiterpene composition in Chinese pinus massoniana oleoresin without the need of said separation.

SUMMARY OF THE INVENTION

The object of the present invention is achieved by the following technical solution. The sesquiterpene fraction at 110–120° C./6 mmHg from Chinese pinus massoniana oleoresin composition undergoes isomerization in the presence of sulfuric acid as catalyst to prepare isolongifolene. After the rectification of the isolongifolene has been completed, there remains a residue in the amount of higher than 15% presented at the bottom of the rectification vessel, which is usually discarded or burned as an industrial waste. According to the present invention, the said residue is separated, re-crystallized and purified to prepare β-caryophyllene alcohol. It has been verified via structure analysis and reaction mechanism studies that the β-caryophyllene as presented in said sesquiterpene fraction, at the presence of catalytic sulfuric acid, has been converted into β-caryophyllene alcohol via rearrangement, transannulation and hydration reactions of β-caryophyllene. The process for the preparation of β-caryophyllene alcohol in accordance with this invention has the advantages of simplified process and higher quality of product, which is a new process for the preparation of β-caryophyllene alcohol.

BEST MODES FOR CARRYING OUT THE INVENTION

EXAMPLE 1

Separation 1245 g of the residue obtained from the bottom of the rectification vessel for the rectification of isolongifolene was added into a 2000 ml three-neck flask. The flask was heated to 160–220° C. under 10 mmHg and the fraction of 150–200° C. was collected. The distillate was kept still for crystallization and then filtered via a Buchner filter after the crystals had been crystallized out from the solution to obtain 879.3 g crystalline β-caryophyllene alcohol (mp. 92.8° C. without thermometer correction).

EXAMPLE 2

Re-crystallization 500 ml of n-hexane was added into 500 g crystalline β-caryophyllene alcohol as obtained in Example 1. The crystalline β-caryophyllene alcohol was dissolved into n-hexane under the condition of being warmed in a 50° C. water bath and then, the solution was filtered under the condition of keeping the temperature. The filtrate was kept still for crystallization and then, the solution was filtered after the crystal had been crystallized out to obtain 440 g of crystalline β-caryophyllene alcohol (mp. 94.2–94.8° C. without thermometer correction). The various spectral data were as follows:

(1) MS (m/e): $M^{30}$ 222, 207, 204, 189, 179, 108, 81 (base).
(2) IR ($cm^{-1}$): 3400 (s, OH), 2950 (s, $CH_2$), 1160 (m, $CH_2$), 1330, 1100, 1059, 1019 (s, C—OH).
(3) $^1H$ NMR (δ ppm): 0.882 (3H, s, $CH_3$), 1.005 (6H, s, $CH_3X$ 2), 1.457–1.888 (14H, m, $CH_2$ X 7), 1.479 (1H, m, OH, disappeared after the addition of $D_2O$), 2.080–2.193 (2H, m, CH X 2).
(4) $^{13}C$ NMR (INEPT, δ ppm): 70.9 (C), 48.8 ($CH_2$), 44.9 (CH), 39.8 (CH), 38.7 ($CH_2$), 37.5 ($CH_2$), 36.8 ($CH_2$), 34.9 (C), 34.8 (C), 34.6 ($CH_2$), 33.3 ($CH_3$), 30.5 ($CH_3$), 22.0 ($CH_2$), 20.9 ($CH_2$).
(5) $^{13}$NMR (OFR, δ ppm): 70.9 (s), 48.8 (t), 44.9 (d), 39.8 (d), 38.7 (t), 37.5 (t), 36.8 (t), 34.9 (s), 34.8 (s), 34.6 (t), 33.3 (q), 30.5 (q), 22.0 (t), 20.9 (t), 20.9 (q).
(6) $^{13}C$ NMR (IGD, δ ppm): 70.9 (1c), 48.8 (1c), 44.9 (1c), 39.8 (1c), 38.7 (1c), 37.5 (1c), 36.8 (1c), 34.9 (1c), 34.8 (1c), 34.6 (1c), 33.3 (1c), 30.5 (1c), 22.0 (1c), 20.9 (2c).

EXAMPLE 3

Purification 200 g re-crystallized β-caryophyllene alcohol was added into a vessel fitted with a reflux device: 400 ml anhydrous ethanol was added thereto and 10 g active charcoal used for the purification of injection solution was added thereto. After being heated and refluxed for 10 minutes on a water bath, the solution was filtered under the condition of keeping the temperature, and the filtrate was kept still for crystallization. The solution was filtered after the crystal had been crystallized out, and the obtained crystal was vacuum dried to obtain 180 g β-caryophyllene alcohol. The opticity of the product $[\alpha]^{20}$ is -7.5° C. (c=10, ethanol).

What is claimed is:

1. A process for preparation of β-caryophyllene alcohol, comprising the steps of isomerizing a sesquiterpene fraction of 110 to 120° C. at 6 mm Hg from Chinese pinus massoniana oleoresin in the presence of a sulfuric acid catalyst to prepare isolongifolene; rectifying said isolongifolene to produce a β-caryophyllene alcohol-containing residue; separating β-caryophyllene alcohol crystals from a distillate of said residue; dissolving said β-caryophyllene alcohol crystals, recrystallizing said β-caryophyllene alcohol, and purifying said recrystallized β-caryophyllene alcohol.

2. The process of claim 1 wherein the separating step is performed by heating said residue at a temperature of 160 to 220° C. under 10 mm Hg and collecting said distillate at 150 to 200° C. under 10 mm Hg.

3. The process of claim 1 wherein n-hexane and elevated temperatures are used to dissolve the β-caryophyllene alcohol crystals prior to recrystallization.

* * * * *